United States Patent [19]

Rinehart, Jr. et al.

[11] 3,954,737

[45] May 4, 1976

[54] ATROPISOMERIC ANSA RING COMPOUNDS

[75] Inventors: Kenneth L. Rinehart, Jr., Urbana, Ill.; Waltraut M. J. Knöll, Vienna, Austria

[73] Assignee: University of Illinois Foundation, Urbana, Ill.

[22] Filed: Apr. 5, 1974

[21] Appl. No.: 458,138

[52] U.S. Cl. .......................... 260/239.3 P; 424/244
[51] Int. Cl.² .............. C07D 498/18; C07D 491/08; C07D 267/00
[58] Field of Search ............................. 260/239.3 P

*Primary Examiner*—Henry R. Jiles
*Assistant Examiner*—Robert T. Bond
*Attorney, Agent, or Firm*—Merriam, Marshall, Shapiro & Klose

[57] ABSTRACT

Biologically active stereoisomeric forms of ansa ring compounds are prepared by heat treatment of a reaction mixture comprising the compound dissolved or suspended in a selected reaction medium and subsequent isolation of the desired isomeric form from the reaction mixture.

6 Claims, No Drawings

ATROPISOMERIC ANSA RING COMPOUNDS

BACKGROUND

The present invention relates generally to biologically active ansa ring compounds and more specifically to biologically active atropisomeric forms of such compounds, to methods for their preparation, to pharmaceutical compositions including such compounds, and to therapeutic methods involving their administration.

Antibiotic or otherwise biologically active ansa ring compounds containing an aliphatic chain "bridge" connecting two nonadjacent positions of an aromatic nucleus are commonly referred to as ansamycins. [See, generally, Rinehart, Accounts Chem. Res., 5, 57(1972)]. Thus far, five generally representative groups within the general class of ansamycins have been identified:

1. Rifamycins, produced from *Streptomyces mediterranei* [Sensi, et al., Farmaco Ed. Sci., 14, 146 (1959)];
2. Streptovanicins, produced from *Streptomyces spectabilis* [Siminoff, et al., Am. Rev. Tuberc. Pulm. Dis., 75, 576 (1957)];
3. Tolypomycins, produced from *Streptomyces tolypophorus* [Kishi, et al., Tetrahedron Lett., 91 (1969); Shibata, et al., J. Antibiot., 24, 810 (1971)];
4. Geldanamycin, produced from *Streptomyces hygroscopicus* var. geldanus var. nova [DeBoer, et al., J. Antibiot., 23, 442 (1970)]; and,
5. Maytansine, produced from *Maytenus ovatus* [See, e.g., Kupchan, et al., J.A.C.S., 94, 1354 (1972)]U.S.

Various derivatives of such ansamycin compounds have been prepared by processes which leave the aliphatic bridge intact (e.g., streptovaricin acylates as described in U. S. patent application Ser. No. 328,727). For the purposes of the present invention, the term "ansa ring compound" shall mean any naturally occurring or synthetically derived ansamycin compound containing an intact aliphatic bridge as above described.

Each ansa ring compound characteristically displays a stereochemical property of "helicity" in much the same manner as complex nucleic acids and certain proteins, i.e., each is wound in a helical or screw-like manner—either in the manner of a right handed threaded screw (hereafter, "P-helicity") or of a left handed threaded screw (hereafter, "M-helicity").

Atropisomerism is generally defined as any type of stereoisomerism due to restricted rotation about single bonds. [See, e.g., Eliel, *Stereochemistry of Carbon Compounds*, McGraw-Hill (1962)]. With respect to ansa ring compounds, the atropisomeric forms would exhibit P-helicity or M-helicity opposite that ordinarily exhibited by the compounds.

BRIEF SUMMARY OF THE INVENTION

According to the present invention biologically active atropisomeric forms of ansa ring compounds are prepared through preparation of a reaction mixture comprising such compounds dissolved or suspended in a selected reaction medium, followed by heat treatment of the reaction mixture and isolation of the desired atropisomer. Further, according to the present invention, pharmaceutical compositions containing such atropisomeric forms are prepared and administered in therapeutic methods for treatment of hosts to bacterial and viral diseases.

DETAILED DESCRIPTION

The present invention may be better understood through consideration of the following descriptions of the preparation of atropisomeric forms of streptovaricins and streptovaricin derivatives.

EXAMPLE I

Preparation of Atropisostreptovaricin C

A. Employing a Pyridine Reaction Medium 154 mg. (0.2 mmole) of streptovaricin C in 12 ml. pyridine were refluxed for three hours. 2 N hydrochloric acid was added and the solution was extracted three times with chloroform. The organic phase was washed with 5% sodium bicarbonate solution and saturated sodium chloride solution, then dried over sodium sulfate and the solvent evaporated. The thin layer chromatogram (chloroform - methanol (95:5)) showed the following substances: streptovaricin C (Rf 0,36); atropisostreptovaricin C (Rf 0,20); atropisostreptovaricin $F_c$ (Rf 0,11); traces of streptovaricin $F_c$ (Rf 0,07); and one byproduct (Rf 0,04). The raw extract was purified by thicklayer chromatography [chloroform-methanol (97:3), three times front] to give 20 mg. of atropisostreptovaricin C (13%) which was separately rechromatographed. (The desired product contained always an UV active impurity Rf 0,26 [chloroform-methanol (95:5)], which could not be removed and which seemed to be a decomposition product).

The desired product was lyophilized from a benzene/t-butanol mixture to yield an orange powder, m.p., 184°–189°C. (corrected, 188°–193°C).
Rotational analysis:
$[\alpha]_D^{23} - 551°$ (chloroform, c = 0,1197) [cf., streptovaricin C, $[\alpha]_D^{23} + 602$]

U.V. and N.M.R. confirmed the proposed structure of the product. The (chloroform) I.R. spectrum revealed the following, which is identical to streptovaricin C except in the fingerprint region as indicated.
3430, 2990, 2940, 1760, 1720, 1655, 1620, 1585, 1545, 1395, 1370, 1360, 1335, 1275, 1130 (cf., streptovaricin C 1120), 1105 (cf., streptovaricin C 1100), 1060 (cf., streptovaricin C 1070) 1030 (cf., streptovaricin C 1040), and 985 (cf. streptovaricin C 995).

The mass spectrum was identical to that of streptovaricin C except the M+ and most of the other peaks for ions with high molecular weight were much weaker than in streptovaricin C. High resolution mass spectrum analysis with peak matching revealed the following:

Analysis Calcd. for $C_{40}H_{51}NO_{14}$: 769.3310
Found: 769.3274

The circular dichroism spectral curve of the product was approximately the mirror image of that of streptovaricin C.

B. Employing a Toluene Reaction Medium 1. 419 mg. of streptovaricin C was dissolved in 30 ml. of toluene and the resulting solution was refluxed overnight. The reaction mixture was evaporated to dryness under reduced pressure and the residual material was then chromatographed over 60 g. of silicic acid in a 25 × 600 mm. column using chloroform-methanol (98:2) to yield 380 mg. of starting material and 10 mg. of atropisostreptovaricin C (M+: m/e 769).

2. 814 mg. of streptovaricin C was refluxed overnight in 50 ml. of toluene. The reaction mixture was evaporated under reduced pressure to give a reddish-orange residue which was chromatographed as above to yield 736 mg. of starting material and 44 mg. of atropisostreptovaricin C.

C. Employing a Xylene Reaction Medium

The 380 mg. of streptovaricin C recovered from preparation B(1), above, was heated under reflux in 30 ml. of xylene for 16 hours. After evaporation of the solvent, the reaction product was examined by thin layer chromatography over silicic acid (0.25 mm. thickness) using chloroform-methanol (95:5) and indicated the formation of numerous complex products. The result suggested that the temperature employed (140°C.) might be too high for formation of substantial amounts of the atropisomeric form without side reactions such as lactonization. No attempt was made to isolate any existing atropisostreptovaricin C from the product.

EXAMPLE II

Preparation of Streptovaricin $F_c$ from Streptovaricin C 80 mg. of streptovaricin C (0.107 mmole), 250 mg. of an air dried basic ion exchange resin (e.g., Dowex 1-X2, OH-form), 6 drops of water and 6 ml. of isopropanol were refluxed for 1.5 hours. The reaction mixture was filtered and the solvent evaporated. The residue was purified by thick layer chromatography (chloroform-methanol, 90:10) to give 35 mg. of starting product and 23 mg. of slightly impure streptovaricin $F_c$ which was rechromatographed and lyophilized from benzene to yield an orange powder, m.p. 208°–211°C., corrected 213°–216°C.

Analysis calcd. for $C_{39}H_{47}NO_{13}$: C,63.49; H,6.42; N,1.90
Found: C,60.81; H,7.10; N,1.93

Rotation analysis:
$[\alpha]_D^{23} = + 630°$ (chloroform, c = 0.0762)
U.V., I.R., and NMR spectra confirmed the proposed structures. High resolution mass spectrum analysis revealed the following:

Analysis calcd. for $C_{39}H_{47}NO_{13}$: 737.3047
Found: 737.3077

EXAMPLE III

Preparation of Atropisostreptovaricin $F_c$ from Streptovaricin $F_c$ 1.0 mg. streptovaricin $F_c$ and 0.5 ml of pyridine was refluxed in the dark for 2.5 hours. The reaction mixture was extracted with chloroform, the organic phase was dried over sodium sulfate and the solvent was evaporated. Thin layer chromatography [chloroform-methanol (97:3), three times front] revealed atropisostreptovaricin $F_c$ (Rf 0.24) as the only product and very little of the starting material (Rf 0.18).

EXAMPLE IV

Preparation of Atropisostreptovaricin $F_c$ from Streptovaricin C.

154 mg. of streptovaricin C (0.2 mmole), 500 mg. of an air dried basic ion exchange resin (e.g., Dowex 1-X2, OH form), 10 drops of water and 10 ml. of pyridine were refluxed in a sealed tube for 14 hrs. The reaction mixture was filtered and the pyridine was distilled off. The red distillation residue was dissolved in water and extracted three times with chloroform. The organic phase was washed once with 2 N hydrochloric acid, 5 percent potassium carbonate solution, and saturated sodium chloride solution, then dried over sodium sulfate. The solvent was evaporated to give 72 mg. of a red resin. Thick layer chromatography of this [chloroform - methanol (97:3), three times front] gave 11 mg. unreacted starting material streptovaricin C (7,1%) (Rf 0,67), 4,7 mg. (3%) atropisostreptovaricin C (Rf 0,46), and 38 mg. (25,7%) atropisostreptovaricin $F_c$ (Rf 0,24), which was crystallized from methanol to give red needles, m.p. 226°–228°C., corrected, 231°–233°C.

Rotational analysis:
$[\alpha]_D^{23} = - 452°$ (chloroform, c - 0,1261)

U.V. and NMR analysis confirmed the proposed structure. I.R. spectral analysis in chloroform revealed the following, which is identical to streptovaricin $F_c$ except in the fingerprint region as indicated and in that streptovaricin $F_c$ has two additional peaks at 1100 and 1040.

3500, 3430, 2930, 2850, 1760 (cf., streptovaricin $F_c$ 1765), 1725, 1665, 1615, 1585, 1540, 1475 (cf., streptovaricin $F_c$ 1485), 1435 (sh), 1375, 1335, 1120, 1060 (cf., streptovaricin $F_c$ 1075), 1005 (cf., streptovaricin $F_c$ 1000), 990 (not in streptovaricin $F_c$), 980.

The mass spectrum was identical with that of streptovaricin $F_c$, except the $M^+$ peak and most of the other peaks for ions with high molecular weight are much weaker than in streptovaricin $F_c$. High resolution mass spectral analysis with peak matching revealed the following:

Analysis calcd. for $C_{39}H_{47}NO_{13}$: 737.3047
Found: 737.3039

The circular dichroism spectral curve of the product was approximately the mirror image of that of streptovaricin $F_c$.

EXAMPLE V

Preparation of Atropisostreptovaricin C Triacetate 50 mg. of streptovaricin C triacetate (prepared through reaction of streptovaricin C in pyridine with acetic anhydride according to the method of U.S. patent application Ser. No. 328,727) was refluxed overnight in 30 ml of benzene. The reaction mixture was evaporated to dryness to give a residue which was purified by thin layer chromatography on silica gel (20 × 20 cm., 1 mm. thickness) using benzene-acetone (7:3) to yield 45 mg. of starting material [rotational anlaysis: $[\alpha]_D^{23} + 448.4°$ (chloroform, c = 0.22)] and 5 mg. of atropisostreptovaricin C triacetate [rotational analysis: $[\alpha]_D^{23} - 558.0°$ (chloroform, c = 0.08)].

EXAMPLE VI

Preparation of Atropisomeric Streptovaricin C Triacetate Cyclic Benzeneboronate

A 50 ml. round-bottomed flask was fitted with a 130 mm. Vigreux column connected to a distilling head with condenser. To the flask was added 225 mg. (0.252 mmole) of streptovaricin C triacetate, 61 mg. (0.50 mmole) of benzeneboronic acid and 30 ml. of 1,4-dioxane. The flask was immersed into an oil bath maintained at 95°C. The system was protected from moisture by means of a drying tube. After 12 hours the bath temperature was increased to 125°C. and 10 ml. of a dioxane-water azeotrope was distilled over a 26-hour period. The reaction was cooled, and the remaining dioxane was removed in vacuo to yield 282 mg. of a deep reddish-orange amorphous solid which was chromatographed over silica gel (60 g.).

Elution with benzene-acetone (17:3) yielded an orange glass which was crystallized from methylene chloride-ether to give 30 mg. (12%) of the cyclized ester as orange needles, m.p. 210°–213°C. An analytical sample of streptovaricin C triacetate cyclic benzeneboronate product was crystallized from methylene chloride-ether, m.p. 212°–215°C.

Analysis calcd. for $C_{52}H_{62}NO_{18}B$: C,62.47; H,6.25; N,1.40
Found: C,62.90; H,6.20; N,1.51

Rotational analysis
$[\alpha]_D^{23} + 279.1°$

Further elution with the same solvent mixture yielded a second orange glass which was crystallized from methylene chloride-ether to give 23 mg. (9 percent) of the cyclized ester as orange needles. An analytical sample of atropisostreptovaricin C triacetate cyclic benzeneboronate product was recrystallized from methylene chloride-ether, m.p. 210°–213°C.

Analysis calcd. for $C_{52}H_{60}NO_{17}B$: C,63.61; H,6.16; N,1.42
Found: C,63.38; H,5.98; N,1.36

Rotational anlaysis:
$[\alpha]_D^{23} - 870.6°$

The circular dichroism spectrum was esentially the mirror image of that of streptovaricin C triacetate cyclic benzeneboronate.

EXAMPLE VII
Preparation of Atropisostreptovaricin C Triacetate Cyclic Bromobenzeneboronate To a round-bottomed flask equipped wth a condenser, Dean-Stark trap and drying tube were added 895 mg. (1.00 mmole) of streptovaricin C triacetate, 401 mg. (2.00 mmole) of p-bromobenzeneboronic acid and 100 ml. of benzene. The mixture was heated to reflux for 18 hours, then cooled. The solvent was removed in vacuo. The residue was chromatographed over 100 g. of silica gel. Elution wth chloroformacetone (17:3) gave 563 mg. of an orange glass which consisted of two compounds. This material was rechromatographed over 130 g. of silica gel. Elution with benzene-acetone (4:1) yielded 275 mg. of the crude cyclized ester which was crystallized from methylene chloride-ether to give 177 mg. (16 percent) of orange needles. An analytical sample of streptovaricin C triacetate cyclic bromobenzeneboronate was recrystallized from methylene chloride-ether, m.p. 215°–220°C.

Analysis Calcd. for $C_{52}H_{61}BBr$: C,57.90; H,5.70; N,1.30
Found: C,58.02; H,5.80; N,1.39

Rotational analysis:
$[\alpha]_D^{26} + 230.9°$.

Further elution with the same solvent mixture yielded 248 mg. of the crude cyclized ester which was crystallized from methylene chloride-ether to give 146 mg. (14%) of orange-colored crystals. An analytical sample of atropisostreptovaricin C triacetate cyclic bromobenzeneboronate was recrystallized from methylene chloride-ether (cubic) as well as from ether (plates), m.p. 214°–217°C. (ether).

Analysis Calcd. for $C_{52}H_{59}NO_{17}BBr$: C,58.88; H,5.61; Br,7.53
Found: C,58.94; H,5.83; Br,7.28

Rotational analysis:
$[\alpha]_D - 516.7°$.

The circular dichroism spectrum was essentially the mirror image of that of streptovaricin C triacetate cyclic bromobenzeneboronate.

Below is a table generally summarizing comparative approximate rotational analyses values for the above-prepared compounds.

TABLE I

| Compound | Analysis |
| --- | --- |
| Streptovaricin C | $[\alpha]_D^{23} + 602°$ |
| Atropisostreptovaricin C | $[\alpha]_D^{23} - 551°$ |
| Streptovaricin $F_c$ | $[\alpha]_D^{23} + 630°$ |
| Atropisostreptovaricin $F_c$ | $[\alpha]_D^{23} - 452°$ |
| Streptovaricin C Triacetate | $[\alpha]_D^{23} + 448°$ |
| Atropisostreptovaricin C Triacetate | $[\alpha]_D^{22} - 558°$ |
| Streptovaricin C Triacetate cyclic benzeneboronate | $[\alpha]_D^{23} + 279°$ |
| Atropisostreptovaricin C Triacetate cyclic benzeneboronate | $[\alpha]_D^{23} - 870°$ |
| Streptovaricin C Triacetate cyclic bromobenzeneboronate | $[\alpha]_D^{26} + 231°$ |
| Atropisostreptovaricin C Triacetate cyclic bromobenzeneboronate | $[\alpha]_D^{26} - 517°$ |

The formulae, below, graphically illustrate the stereoisomeric similarities and differences between streptovaricin C and atropisostreptovaricin C. The formulae below, similarly relate to streptovaricin $F_c$ and atropisostreptovaricin $F_c$.

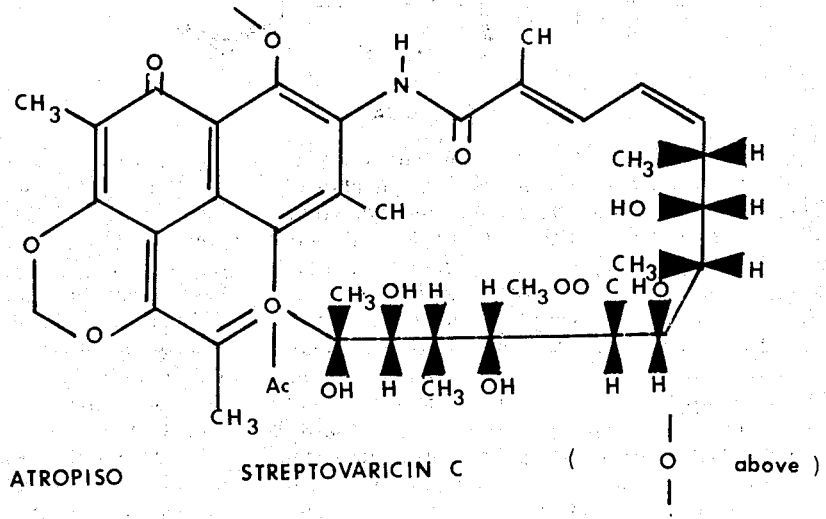

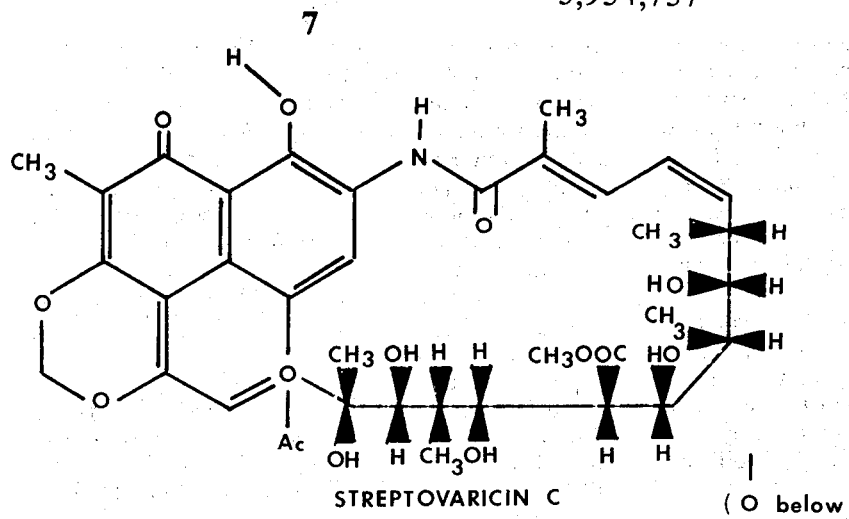

STREPTOVARICIN C

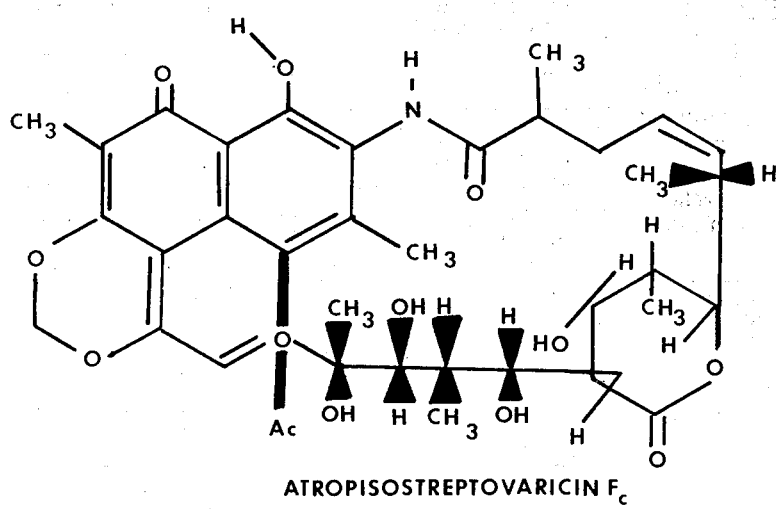

ATROPISOSTREPTOVARICIN F_c

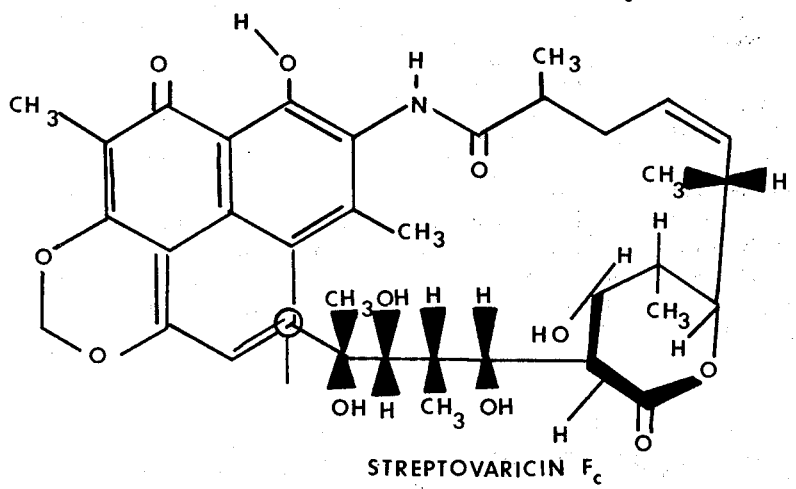

STREPTOVARICIN F_c

As may be seen from the above preparations, the selection of a reaction medium for use in preparation of atropisomeric forms of ansa ring compounds according to the invention may be made without difficult from within the class of common organic aromatic and aliphatic solvents. Among the criteria suggested for use in the selection process is consideration of the boiling point of the medium where heating is to proceed under reflux due to the fact that a medium having a boiling point nearly equal to or in excess of the melting point of the particular compound might ordinarily be avoided. (See, e.g., Example I(C), above.) Ordinarily such common media as benzene, toluene, xylene, dioxane, pyridine, tetrahydrofuran, and cyclohexane may be employed without adverse effects.

While it is desirable to carry out the heating process involving the particular ansa ring compound with the compound in solution, it is expected that heating with the compound suspended in the selected medium will yield acceptable results.

While the above examples generally illustrate heating at reaction medium refluxing temperatures at atmospheric pressure, heating at lower temperatures is certainly contemplated as is heating at higher temperatures under greater than atmospheric pressure.

Isolation of the desired atropisomeric ansa ring compounds may proceed by commonly accepted techniques, such as thin layer chromatography, column chromatography, gas-liquid chromatography, high pressure liquid chromatography, countercurrent distribution and crystallization.

Tables II, III and IV below respectively set forth activities of representative atropisomeric forms of ansa ring compounds of the invention relative to the "normal" isomeric forms in the following assays: (A) reverse transcriptase (RNA-directed DNA polymerase); (B) bacterial RNA polymerase; (C) B. subtilis bacterial inhibition; (D) S. lutea bacterial inhibition; and, inhibition of numerous other bacterial strains.

The assay and work-up conditions for reverse transcriptase analysis were essentially those described by Brockman, et al., (Nature, 230, 249, (1971)), except for eliminating the phosphate from the washing solution (10 percent trichloroacetic acid).

The assay for bacterial RNA polymerase followed the procedure of Reusser (J. Bacteriol, 105, 580 (1971)). Assay mixtures were prepared containing in a total volume of 0.25 ml: Tris-hydrochloride buffer, pH 7.9, 5 $\mu$moles; $MgCl_2$, 1 $\mu$mole; mercaptoethanol, 3 $\mu$moles; $MnCl_2$, 0.25 $\mu$mole; quanosine triphosphate, cytidine triphosphate, uridine triphosphate, 0.1 $\mu$mole each; adenosine triphosphate 8-$^{14}$C, 0.1 $\mu$mole containing 0.05 $\mu$Ci; dAT, 0.2 units; polymerase, ~35 $\mu$g. The reaction mixtures were incubated at 30°C for 15 min.

The assay for B. subtilis bacterial inhibition was obtained on plates with B. subtilis UC 564 spores in agar with the following composition per liter:

| | |
|---|---|
| $Na_2HPO_4.7H_2O$ | 1.7 gm |
| $KH_2PO_4$ | 2.0 gm |
| $MgSO_4$ | 0.1 gm |
| $(NH_4)_2SO_4$ | 1.0 gm |
| Agar | 15 gm |

After autoclaving, 10 ml. of 20 percent glucose was added. The seeding rate was approximately $10^9$ spores per liter. Test solutions were applied to ½ inch paper discs (Schleicher & Schuell 740E) with 0.08 ml. per disc. Zones of inhibition were recorded.

The assay for S. lutea inhibition was as follows. Water-soluble preparations were dissolved in brain heart infusion broth (Difco) to 1 mg./ml. Water-insoluble preparations were dissolved (or suspended) in dimethylformamide to 10 mg./ml. and diluted with brain heart broth to 1 mg./ml. Two-fold serial dilutions were made with broth starting with 1 mg./ml. with final volumes of 0.1 ml. per dilution. Overnight bacterial cultures were diluted 1:20,000 with brain heart and 0.1 ml. of diluted culture was added to each dilution of antibiotic (final total volume was 0.2 ml.). This was all done in plastic microtest plates (Microtest II Tissue Culture Plate, Bioquest). The plates were incubated at 37° for 16–18 hours and zones of inhibition were recorded.

Assays for inhibition of other bacterial strains were carried out according to standard uniform procedures.

TABLE II

| Compound | Reverse Transcriptase % Inhibition |
|---|---|
| Streptovaricin C | 31–53 |
| Atropisostreptovaricin C | 70 |
| Streptovaricin $F_c$ | 68 |
| Atropisostreptovaricin $F_c$ | 54 |

TABLE III

| Compound | E.Coli RNA Polymerase % Inhibition |
|---|---|
| Streptovaricin C | 78 |
| Atropisostreptovaricin C | 50 |
| Streptovaricin $F_c$ | 0 |
| Atropisostreptovaricin $F_c$ | 0 |

TABLE V

| Bacteria | Bacterial Growth Inhibition Compound, Zone of Inhibition (mm.)* | | | |
|---|---|---|---|---|
| | SvC | A-SvC | $SvF_c$ | $A-SvF_c$ |
| B. substilis | 22 | 14 | 0 | 0 |
| S. aureus | 26 | 20 | 0 | 0 |
| S. lutea | 33 | 28 | 0 | 0 |
| K. pneumoniae | 21 | 0 | 0 | 0 |
| E. coli | 13 | 0 | 0 | 0 |
| S. schottmuelleri | 10 | 0 | 0 | 0 |
| P. vulgaris | 8 | 0 | 0 | 0 |
| M. avium | 15 | 20 | 14 | 0 |
| P. oxalicum | 0 | 0 | 0 | 0 |
| S. pasteurianum | — | 0 | 0 | 0 |
| B. cereus | — | 9 | 0 | 0 |
| P. aeruginosa | — | 0 | 0 | 0 |

*(SvC = streptovaricin C; A-Svc = atropisostreptovaricin C; $SvF_c$ = streptovaricin $F_c$; and, $A-SvF_c$ = atropisostreptovaricin $F_c$.)

TABLE IIA

| Compound | Reverse Transcriptose % Inhibition |
|---|---|
| Streptovaricin C Triacetate Cyclic Benzeneboronate | 44 |
| Atropisostreptovaricin C Triacetate Cyclic Benzeneboronate | 77 |
| Streptovaricin C Triacetate Cyclic p-Bromobenzeneboronate | 57 |
| Atropisostreptovaricin C Triacetate Cyclic p-Bromobenzeneboronate | 66 |

Table IIIA

| Compound | E. Coli RNA Polymerase % Inhibition |
|---|---|
| Streptovaricin C Triacetate Cyclic Benzeneboronate | 2 |
| Atropisostreptovaricin C Triacetate Cyclic Benzeneboronate | 23 |
| Streptovaricin C Triacetate Cyclic p-Bromobenzeneboronate | 20 |
| Atropisostreptovaricin C Triacetate Cyclic p-Bromobenzeneboronate | 46 |

Pharmaceutical compositions of the present invention comprise a minor proportion of one of the atropisomeric ansa ring compounds and a major proportion of a carrier or diluent. The nature of the composition and the carrier or diluent will, of course, depend on the desired route of administration, i.e., orally or parenterally.

Thus, for example, antibacterial and antiviral pharmaceutical compositions could be prepared in the form of compressed tablets, powders, granules, capsules, aqueous solution suspensions in edible oils, aqueous solutions or other dosage forms which are particularly useful for oral administration. Similarly, liquid preparations or formulations may be employed for parenteral use in a medium including a sterile solvent or a sterile suspending vehicle containing an injectable oil, or water-containing hydrophilic colloids such as sodium carboxymethyl cellulose, methyl cellulose, polyvinylpyrrolidone, gelatine, tragacanth and the like.

Antibacterial and antiviral pharmaceutical compositions might also take the form of topical preparations such as ointments and aerosol sprays. They may also include other compatible therapeutic agents.

In the use of compounds of the present invention for the treatment of diseases of viral origin, contact between the compounds and a tumor may be accomplished by dissolving the compounds in a suitable solvent, e.g., aqueous DMSO, ethanol, methanol, chloroform, acetone, methylene chloride, and ethyl acetate and introducing the solution directly or indirectly into the environment of the disease.

The concentration of the compounds in the environment of the disease may be from 20 mcg./ml. to 400 mcg./ml. with from 20 mcg./ml. to 50 mcg./ml. being preferred.

The amount of the compound to be administered for a given antibacterial, or antiviral activity depends on the species, age, and weight of the host as well as the particular conditions to be treated and the route of administration. In general, the parenteral dose expressed as the total amount of the compound is from about 5 to 50 mg./kg. body weight. An oral dose is from about 1 to 10 times the parenteral dose or from 50 to 500 mg./kg. body weight given 1 to 4 times daily.

The following table indicates dosages, for various species (adult):

| Species | Parenteral (mg./kg./day) | Oral (mg./kg./day) |
|---|---|---|
| Dogs | 5 to 50 | 20 to 500 |
| Cats | 5 to 50 | 20 to 500 |
| Rats | 30 to 100 | 100 to 500 |
| Mice | 30 to 100 | 100 to 500 |
| Human | 5 to 100 | 20 to 500 |

The therapeutic methods of the present invention comprise administration of effective amounts of the above mentioned pharmaceutical compositions to a host afflicted with a bacterial or viral disease. The foregoing detailed description has been given for clearness of understanding only, and no unnescessary limitations should be understood therefrom, as modifications will be obvious to those skilled in the art.

What is claimed is:

1. A method for preparing the atropisomeric form of a selected streptovaricin compound, said method comprising:
    preparing a reaction mixture through dissolving or suspending the said compound in a selected reaction medium;
    heat treating said reaction mixture at a temperature below the melting point of said compound and sufficient to promote formation of the atropisomeric form of said compound; and,
    isolating the atropisomeric form of said compound from the reaction mixture.
2. The compound, astropisostreptovaricin C.
3. The compound, atropisostreptovaricin $F_c$.
4. The compound, atropisostreptovaricin C triacetate.
5. The compound, atropisostreptovaricin C triacetate cyclic benzeneboronate.
6. The compound, atropisostreptovaricin C triacetate cyclic bromobenzeneboronate.

* * * * *